(12) United States Patent
Zipprich

(10) Patent No.: US 8,801,434 B2
(45) Date of Patent: Aug. 12, 2014

(54) LABORATORY IMPLANT

(76) Inventor: Holger Zipprich, Darmstadt (DE)

( * ) Notice: Subject to any disclaimer, the term of this patent is extended or adjusted under 35 U.S.C. 154(b) by 645 days.

(21) Appl. No.: 12/665,649

(22) PCT Filed: Nov. 2, 2007

(86) PCT No.: PCT/EP2007/009525
§ 371 (c)(1),
(2), (4) Date: Jun. 15, 2010

(87) PCT Pub. No.: WO2008/154947
PCT Pub. Date: Dec. 24, 2008

(65) Prior Publication Data
US 2010/0304337 A1 Dec. 2, 2010

(30) Foreign Application Priority Data

Jun. 21, 2007 (DE) .......................... 10 2007 029 105

(51) Int. Cl.
*A61C 3/00* (2006.01)
(52) U.S. Cl.
USPC ........................................................ 433/152
(58) Field of Classification Search
CPC ... A61C 13/0003; A61C 8/005; A61C 8/0053
USPC ........... 433/201, 172, 173, 174, 202.1, 203.1, 433/44, 75, 141, 152
See application file for complete search history.

(56) References Cited

U.S. PATENT DOCUMENTS

| 3,964,937 | A | * | 6/1976 | Post et al. ...................... 148/210 |
| 5,934,906 | A | * | 8/1999 | Phimmasone ................ 433/172 |
| 6,116,904 | A | * | 9/2000 | Kirsch et al. .................. 433/173 |

FOREIGN PATENT DOCUMENTS

DE 196 33 570 1/1998

OTHER PUBLICATIONS

International Search Report for PCT/EP2007/009525 mailed Apr. 28, 2008.

* cited by examiner

*Primary Examiner* — Cris L Rodriguez
*Assistant Examiner* — Mirayda A Aponte
(74) *Attorney, Agent, or Firm* — Suzannah K. Sundby, Esq.; Canady + Lortz LLP

(57) ABSTRACT

A method for the production of a dental implant with a post part which can be introduced into a jawbone and with a mounting part assigned thereto, on which a dental prosthetic piece can be mounted, is to allow the dental technician to perform a simple indexing of the mounting part while drawing on current procedural steps. For this purpose, the apical end of the mounting part is shaped in order to adapt the external cross-section of the mounting part to the internal cross-section of the post part.

3 Claims, 14 Drawing Sheets

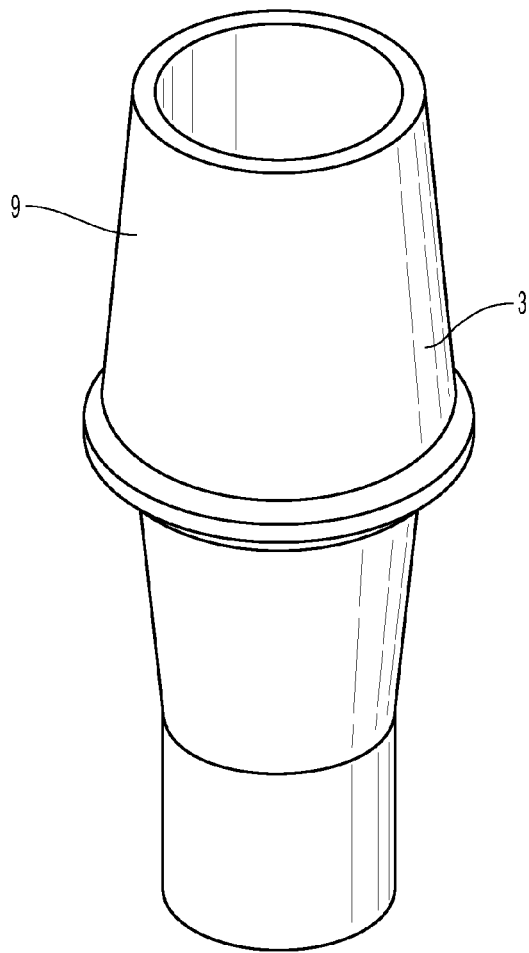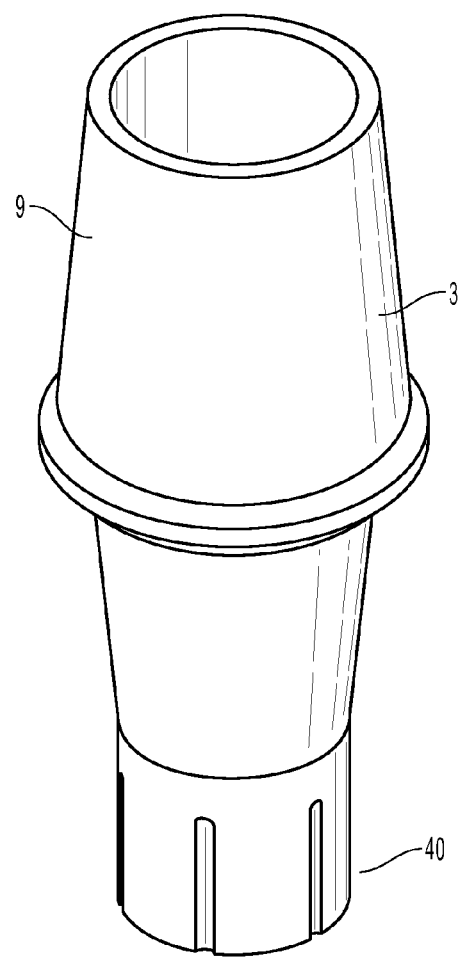
*Fig. 13*
*Fig. 14*

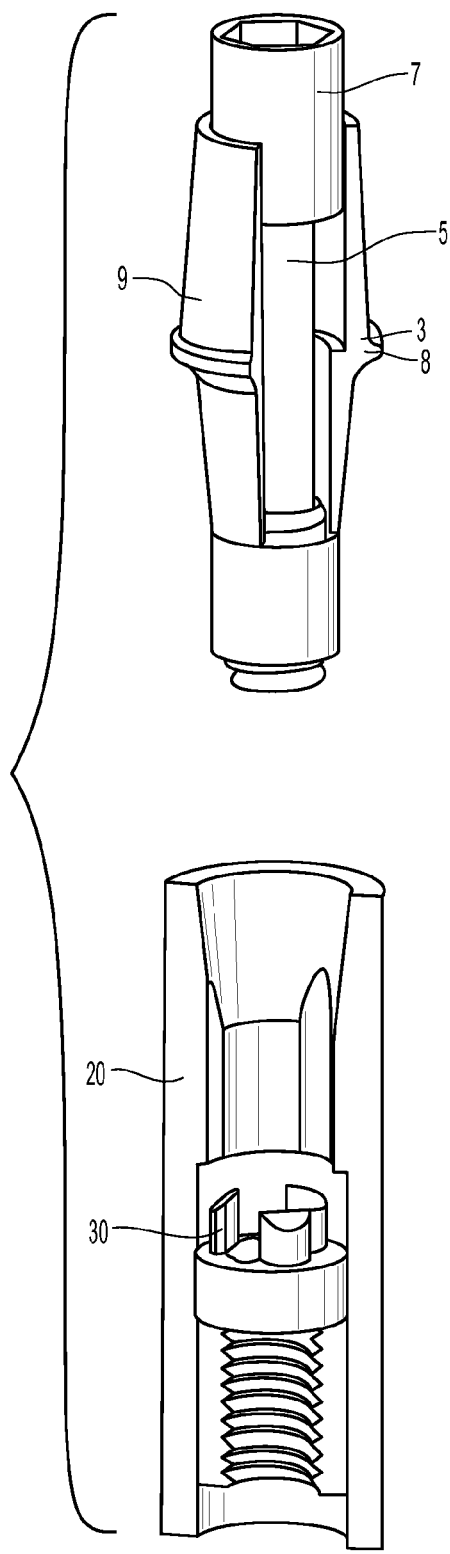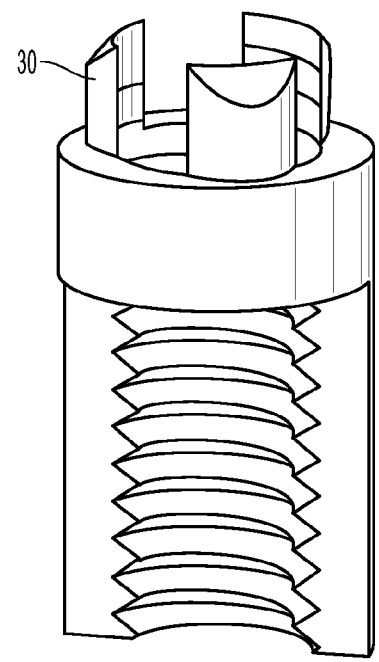
*Fig. 16B*
*Fig. 16A*

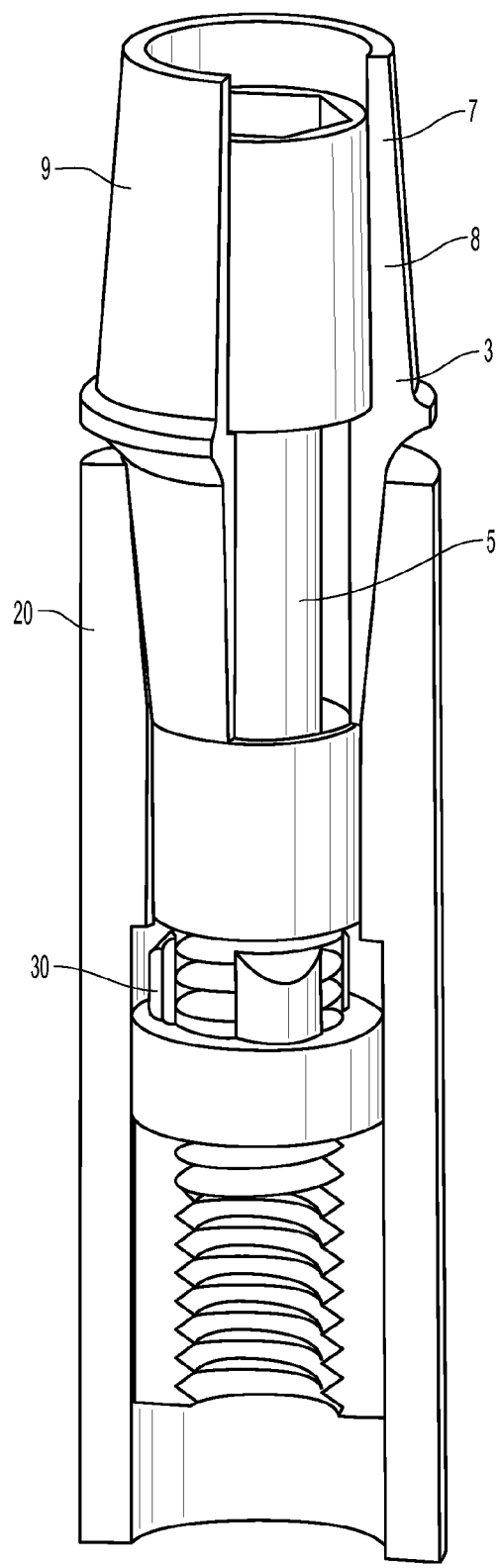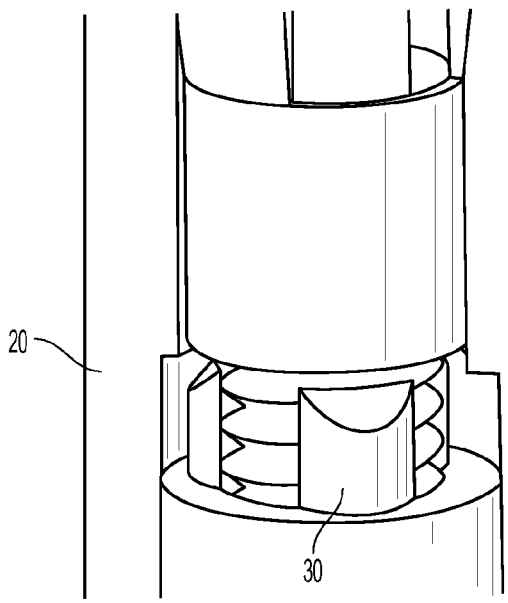
*Fig. 17B*
*Fig. 17A*

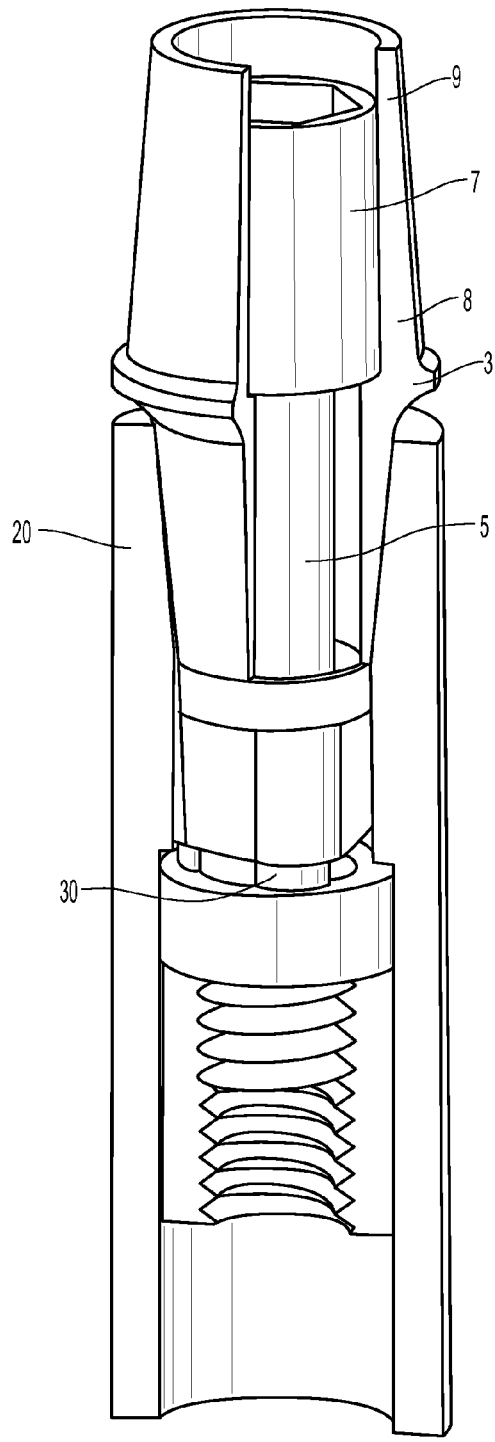
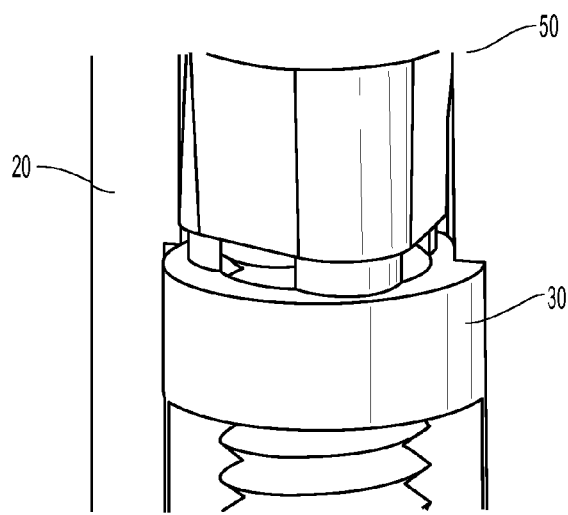
Fig. 18B
Fig. 18A

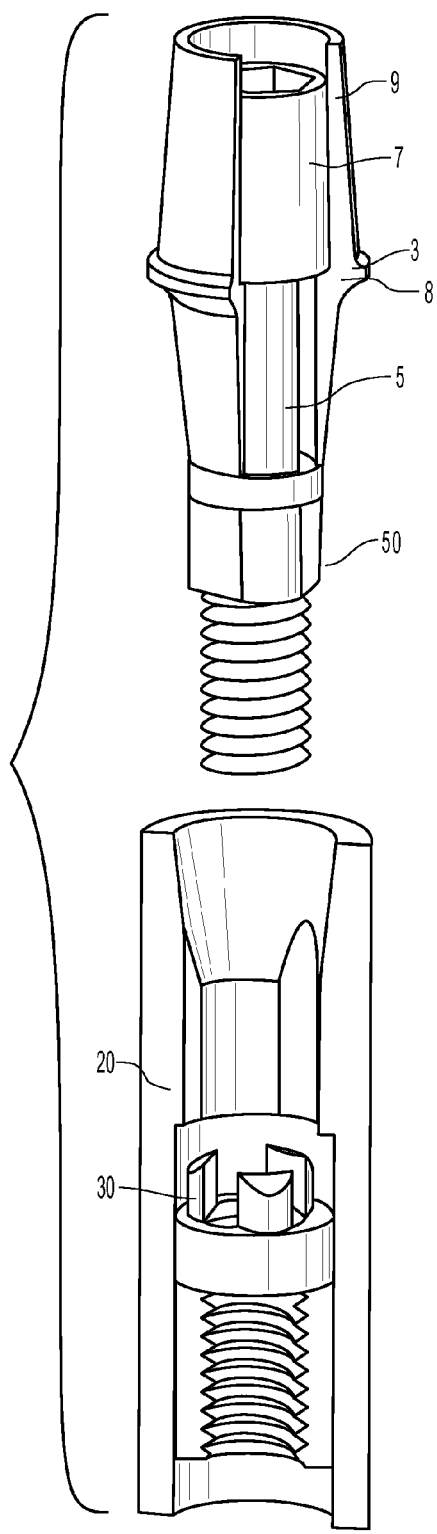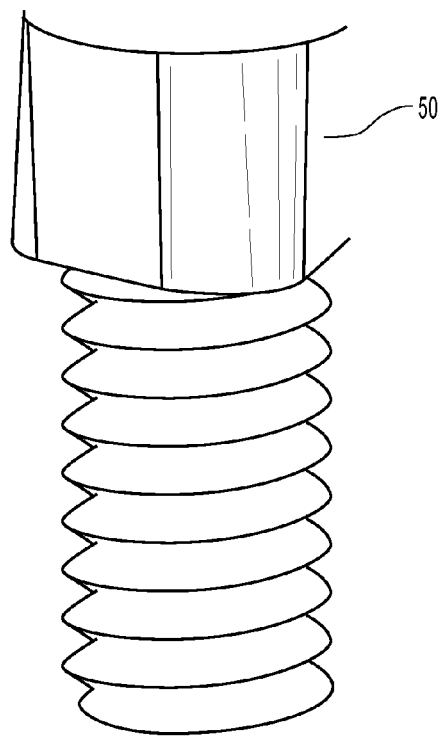
*Fig. 19B*
*Fig. 19A*

LABORATORY IMPLANT

The invention relates to a method for the production of a dental implant with a post part which can be introduced into a jaw bone and with a mounting part assigned thereto on which a dental prosthesis piece can be mounted, and to a laboratory implant for working on a mounting part of this type.

Dental implants are known in various forms. They are usually inserted by screwing into the jawbone in place of a tooth which has been extracted or has fallen out, in order to hold there, after a healing in phase of from three to four months, a prosthetic mounting part which serves as a dental prosthesis, or a crown. For this, such a dental implant is conventionally constructed as a suitably shaped metal body and is shaped in the manner of a pin, and has at the apical end a usually self-tapping screw thread with which the pin is inserted into the appropriately prepared implant bed.

An example of a dental implant of the abovementioned type is shown in FIG. 1 in a partial view and partially in an axial section and in FIG. 2 as an exploded drawing. The two-part dental implant 1 comprises a post part 2 and a mounting part 3. The post part 2, like the head or mounting part 3, is made of metal or a ceramic, and indeed in particular of titanium, a titanium alloy, a titanium-containing alloy, a zirconium oxide or aluminium oxide ceramic or a ceramic which contains either zirconium oxide or aluminium oxide. The post part 2 is provided externally with a thread 4, which can be configured as a self-tapping thread or as a thread which is not self-tapping. The pitch of the thread can be uniform or variable in configuration. The outer form of the post part 2 can also be configured without a thread, with and without mechanical retention aids. The post part 2 and the mounting part 3 are screwed to one another via a connecting screw 5. For this, the thread of the connecting screw 5 is screwed into an internal thread 6 of the post part 2. When the connecting screw 5 is screwed in, the screw head 7 of the connecting screw 5 presses the mounting part 3 on to the post part 2 via the front indentation 8 of the mounting part 3.

The post part 2 is anchored in an appropriately prepared implant bed of the jawbone. The thread construction here ensures a high primary stability and a uniform transmission of the forces which arise during chewing into the jawbone. The mounting part 3 is connected in the upper region 9 to a crown, another prosthetic care item or the like in a manner known per se.

This connection can be configured as screwing, clamping, conical self-locking, vacuum. magnet, ball-head system, cementing, gluing or the like.

In order to counteract rotation or twisting between the mounting part 3 and the post part 2 due to external forces (usually caused by chewing), either mechanical indexing in the form of a mechanical barrier is used, or the surface pressure between the mounting part 3 and the post part 2 is suitably chosen.

The mechanical barrier used for indexing and for avoiding rotation of the mounting part 3 on the post part 2 can be configured in various variants. For this, in the example according to FIGS. 1 and 2 a hexagon socket is provided in the post part 2 and a hexagon insert is provided on the mounting part 3, it also being possible for the configuration as hexagon insert and socket to be the reverse. The number of edges of such an edge system can vary. Furthermore, the corners of such edge systems can be provided with a radius. Torx and polygon systems with a varying number of elements and varying geometry are known as further embodiments. In an alternative embodiment, as shown in FIG. 3, indexings by means of milled cuts 14 in the post part 2 and projecting elements 15 or cams on the mounting part 3 are moreover known.

Rotation between the post part 2 and the mounting part 3 is avoided here via the pressing force of the connecting screw. In addition or alternatively, the connection between the post part 2 and the mounting part 3 can be configured mostly conically. In particular, these are embodiments of the type shown in FIG. 4, which are configured as a conical catch or conical self-locking catch on the basis of the taper and the surface friction between the conical contact surfaces of the post part 2 and the mounting part 3 when the connecting screw 5 is tightened via the conical contact points between the post part 2 and the mounting part 3.

Depending on the insertion position (front teeth or back teeth region, lower jaw, upper jaw), the bone substance, the remaining teeth, the course and position of the vessels and nerves, the person performing the treatment is not always able to drill the bore for the post part/implant to coincide with the axis of the prosthetic care item (crown or the like). It follows from this that a post part/implant of straight configuration and a mounting part of straight configuration do not meet the anatomical circumstances of the patient. To counteract this problem, angled mounting parts are used (FIG. 5). Angled mounting parts are also called angulated mounting parts. FIG. 5 shows a dental implant 1 with a post part 2 and an angled/angulated mounting part 3, wherein the post part 2 and the angulated mounting part 3 are screwed to one another via the connecting screw 5.

This angle is conventionally between 10° and 30°. After the insertion, preferably after the healing in of the post parts, the spatial and geometric information of the remaining teeth (e.g. antagonists, teeth mesially and distally from the insertion position), the mucous membrane and the post part/implant or the assembled mounting part must be determined for production of the crown, bridge or the like. This spatial and geometric information is necessary in order to produce the crown, bridge or the like in an exact fit and in an anatomically optimized manner. For this purpose, an impression, preferably of silicone or another dental impression material, of the situation in the mouth is produced. A cast is preferably made from this impression with gypsum or another dental modelling material. This gypsum model is a duplicate of the situation in the patient's mouth. It provides the dentist or the dental technician with information about the position of the remaining teeth, the mucous membrane and the post parts/implant inserted.

To improve the transfer of the position and geometry of the post parts/implants inserted, special impression posts of metal and/or plastic are preferably pushed and/or screwed on to the post part/implant inserted. The impression is then produced in the mouth, preferably with silicone. After curing of the impression material, when the impression is removed the impression posts either remain on the implant or are removed with the impression. When the cast is made from the impression, the impression posts/mounting posts must be placed in the impression and connected to a laboratory implant. This laboratory implant has the same or a similar geometric form to the inserted post part/implant with respect to the connection and geometrically in the direction of the impression post/mounting post. After the cast has been made from the impression with the integrated impression posts/mounting posts and integrated laboratory implant, a gypsum model with the embedded laboratory implant is obtained.

If the implant system used has indexing, this has been transferred from the patient's mouth to the gypsum model. The prosthetic care item of the implant/implants is planned and produced on the basis of this gypsum model. The rotatory position of the mounting part on the implant plays a decisive role here. If the implant system used has indexing, the positioning possibilities of the mounting part on the laboratory implant are limited. In the case of a hexagon connection, there are six positioning possibilities. In the case of an implant system without indexing, all positions between 0° and 360° can be used. After production, a trial in the patient's mouth is usually undertaken. During this trial or the final integration of the dental prosthesis, the person performing the treatment must integrate the mounting part/the mounting parts and all other prosthetic elements in the patient's mouth in the same position as on the gypsum model.

If the implant system inserted is equipped with indexing, the person performing the treatment has a limited number of possible choices for determining the desired position. If no indexing exists with the implant system used, the person performing the treatment cannot use the advantage of limited positioning to determine the desired position. The person performing the treatment must determine the information about the desired rotatory position(s) of the mounting part(s) on the implant(s) in another way. For this, individual keys are usually produced by the dental technician. The individual key is assembled on the mounting parts/the mounting part and placed as a whole on the implants with the aid of the adjacent teeth and/or the adjacent anatomical structure. After the mounting parts have been fixed on the implants (screwing, cementing etc.), the individual key can be removed and the remaining integration of the prosthetic components can take place. In conclusion, it can be said that for optimized production of the prosthetic components it is advantageous if the dental technician is not limited in the choice of the rotatory positioning by indexing in the connection of the mounting part and the implant. If an individual key has to be produced, however, for the dental technician this is associated with outlay and costs. Furthermore, for the person performing the treatment the integration is associated with a higher outlay. For the dentist, it is more favourable if the number of positioning possibilities of the mounting part on the implant is as low as possible. Eight to twelve possibilities are acceptable, advantageously 3-5 possibilities, but in particular 1-2 positioning possibilities.

It is therefore desirable for the dental technician to be able to use an infinitely variable rotatory freedom of movement of the angulated or non-angulated mounting part/parts of 360°, but for the dentist, without an aid for integration of the one-part or multi-part mounting part in the manner of indexing, to have only a small number of positioning possibilities on the post part in the patient's mouth, so that expensive alignment and positioning during the actual treatment, that is to say in the patient's mouth, can be omitted.

The invention is therefore based on the object of providing a method for the production of a dental implant of the aforementioned type which makes it possible for the dental technician to perform a simple indexing of the mounting part while drawing on current procedures.

This object is achieved according to the invention in that the mounting part is shaped at its apical end to adapt its external cross-section to the internal cross-section of the post part.

As a result of the moulding of the occlusal end of the second mounting part, in addition to the required provision of the necessary tools, a further additional production step by the dental technician is required. Therefore, in a particularly favourable embodiment, the usual operating procedure of the dental technician should not, or should hardly be impaired or altered. For this purpose, a laboratory implant is used in the gypsum model for preparing, for example, the mounting part, the superstructure, the bridge or the crown, instead of the post part which is introduced into the bone. Laboratory implants of this type are currently formed in one piece. The dental technician introduces the mounting part into the laboratory implant and can use, or not, an indexing depending on the laboratory implant or the mounting part. If the laboratory implant is configured as a cutting and/or shaping tool or contains an additional tool which has cutting and/or shaping characteristics, the indexing can take place while the mounting part is screwed or attached to the laboratory implant. Therefore, in a particularly advantageous embodiment, the laboratory implant is formed in several parts.

In this manner, the dental technician can establish the rotatory position of the mounting part relative to the post part and can then apply the indexing to, or finish the indexing on the mounting part while attaching, fixing, screwing in and/or tightly screwing the mounting part. In order to facilitate the shaping and/or the machining of the mounting part, an additional component consisting of a relatively soft material, preferably a plastics material can be fitted to the mounting part, which additional component is preferably only used for indexing.

Depending on the embodiment of the laboratory implant, the dental technician can initially insert the mounting part to the desired depth in the laboratory implant and can then establish the rotatory alignment of the mounting part. Subsequently, by screwing the mounting part together with the laboratory implant, a corresponding tool for shaping and/or machining the mounting part is guided from below up to said mounting part. This tool which is in the laboratory implant must be coordinated in respect of its shaping and/or cutting configuration with the geometric requirements of the indexing in the post part. The indexing of the post and mounting parts can be configured in this respect such that an explicit or ambivalent positioning of the mounting part on the post part is possible.

The tool introduced into the laboratory implant is secured rotatorily in the implant. In so doing, the geometry of the tool is determined using a moulding part. A moulding part of this type transfers the shape of the internal cross-section of the post part to the tool located in the implant. In a particularly advantageous embodiment, the moulding part is indexed to a longer extent in the coronal direction than the actual post part. However, it is also possible to use other methods for aligning and positioning the tool.

Alternatively, the laboratory implant can be constructed such that it is itself configured as a machining tool. In this case, it preferably consists of metal, hard metal or a ceramic material. Otherwise, the tool configured separately in the laboratory implant for producing the indexing is preferably made of a metal, hard metal or a ceramic material. To facilitate the indexing of the mounting part, the cutting edges of the tool are ground and the material thereof has a degree of hardness greater than grade 5 titanium. If the laboratory implant is itself not configured as a machining tool, the tool can be movable or can be fixed in or on the laboratory implant by a detachable or undetachable connection.

In a particularly user-friendly variation, the shaping and/or cutting tool is mounted by a spring in the implant. In this case, the tool preferably has a central hole provided with a thread. If there is no thread in the tool, the tool should be connected at its lower end remote from the cutting tool to a further component in which a thread is present. The mounting part can be screwed into the tool in this thread and, as the screwing action is further intensified, the tool can act in a cutting and/or shaping manner.

In order to integrate the indexed mounting part with absolutely no risk of confusion, a clear allocation of the mounting part to the corresponding post part is required. This can be achieved in that, during the shaping of the mounting part, the indexing of the post part is preferably transferred to the laboratory implant and/or to an additional tool, which can move in translatory manner relative to the axis of the implant. If many possibilities exist for positioning the mounting part on the post part, it is possible that the person performing the treatment will not immediately find the correct position in the patient's mouth. Re-positioning in the patient's mouth may be necessary. The person performing the treatment partly introduces the mounting part into the post part and then has to rotate the mounting part until the engagement of the mounting part matches that of the post part and the mounting part can be brought into the end position. In this process, there is a danger of the mounting part tilting in the post part. If there are at least three indexings in the post part and in the mounting part, the risk of tilting when the mounting part is incorporated is smaller, as is the risk of twisting. The number of indexings and thus, where there is the same angular pitch of the indexings, the number of positioning possibilities as well is preferably less than six and in particular exactly three. To allow only one positioning possibility of the mounting part on the post part, it is also possible to configure more than one indexing, preferably three and to select the angular pitch such that it is not regular. In FIG. 3, the three indexings are distributed equidistantly over the periphery of the post part and of the mounting part, and thus have an offset of 120°. Three positioning possibilities are thus provided for a mounting part of this type. If the spacings are divided up irregularly (for example 100°, 110° and 150°), only one possible positioning of the mounting part on the post part is provided. This can also be achieved with two or more than three indexings.

The indexing position of the post part is transferred onto the laboratory implant in the gypsum model by means of a moulded post which has a previously formed indexing. If the indexing which is integrally formed apically on the moulded post is merely just as long as the tube integrally formed apically on the mounting part or the tube indexed after moulding, the moulded post cannot directly engage in the indexing of the movable tool while being pressed into the implant. The indexing of the tool can only engage in the mounting part when the tool is moved by the force of the connecting screw against the resilience in the direction of the moulded part. In so doing, the danger arises that the moulded part will be deformed and the rotary position transfer will be distorted. To prevent this happening, the indexing of the moulded part should be longer than the tube to be indexed which is integrally formed apically on the mounting part. The difference in length should be at least 0.5 mm, preferably more than 1 mm and, in a particularly preferred variant, more than 2 mm.

An embodiment of the invention will be described in detail with reference to the drawings, in which.

Figure 3:
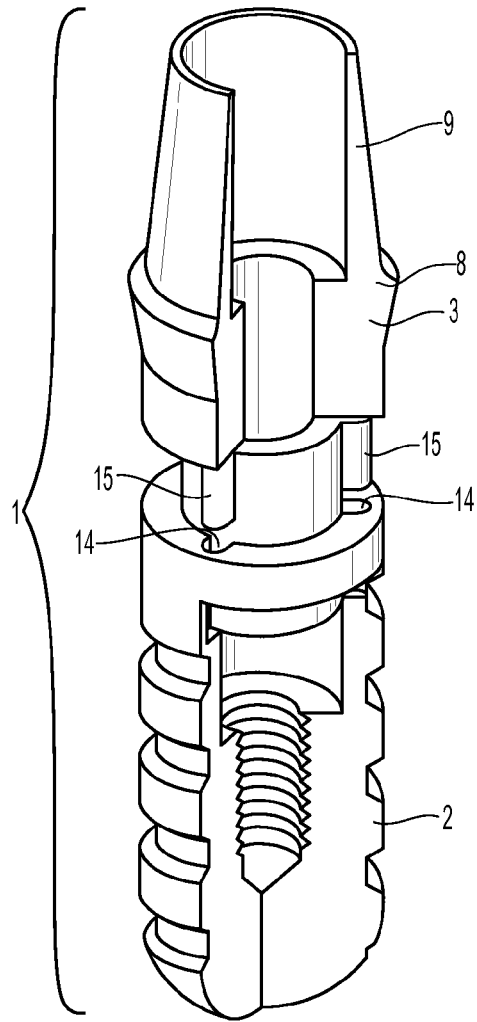
Figure 4:
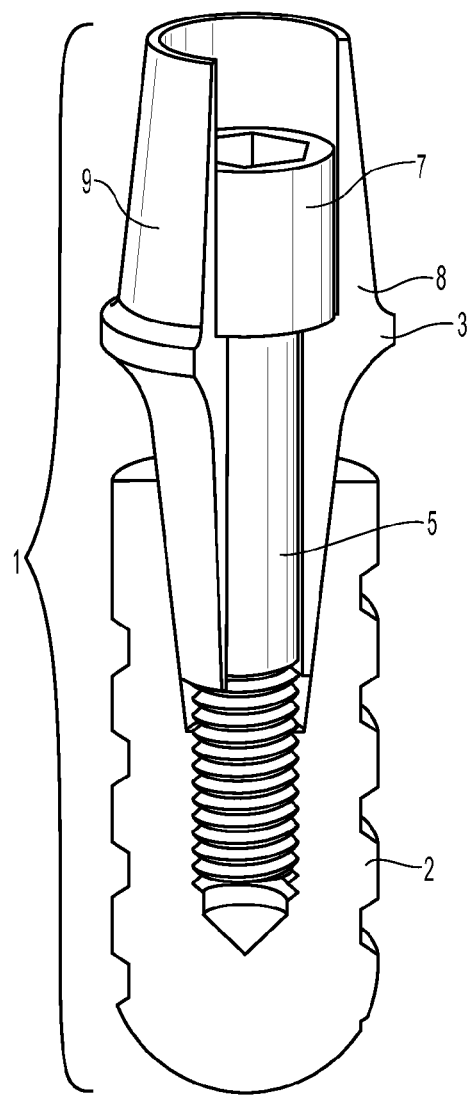
Figures 5, 6:
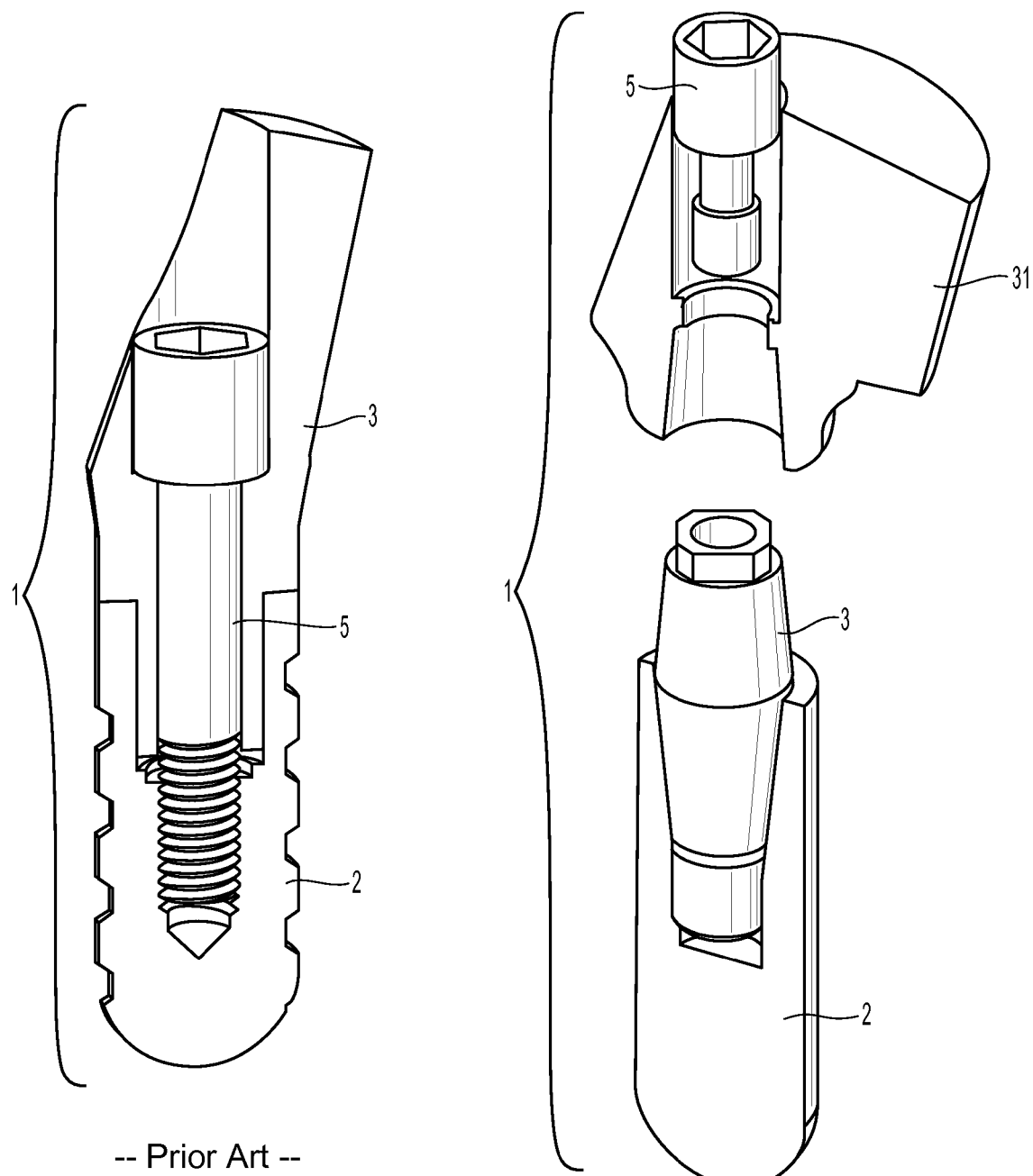
Figure 7:
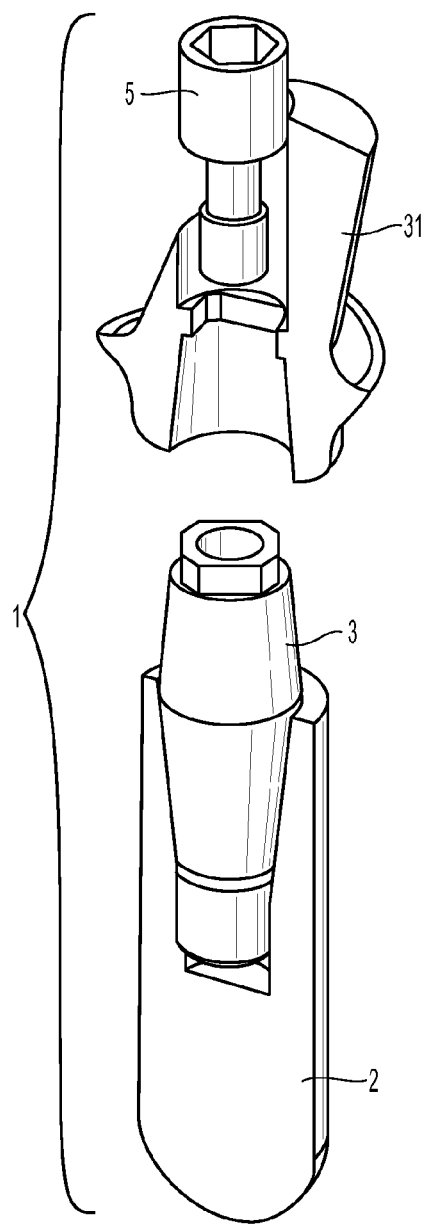
Figure 8:
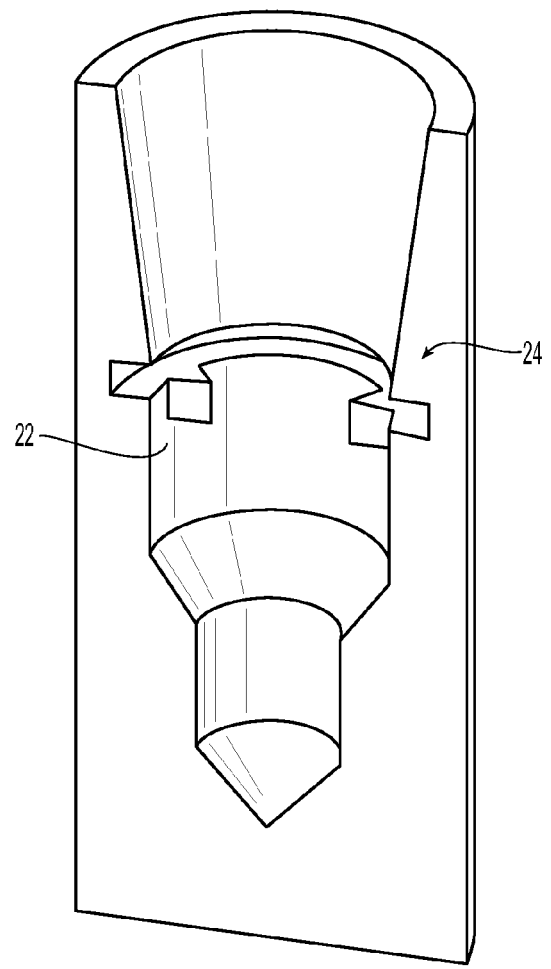
Figures 9, 10:
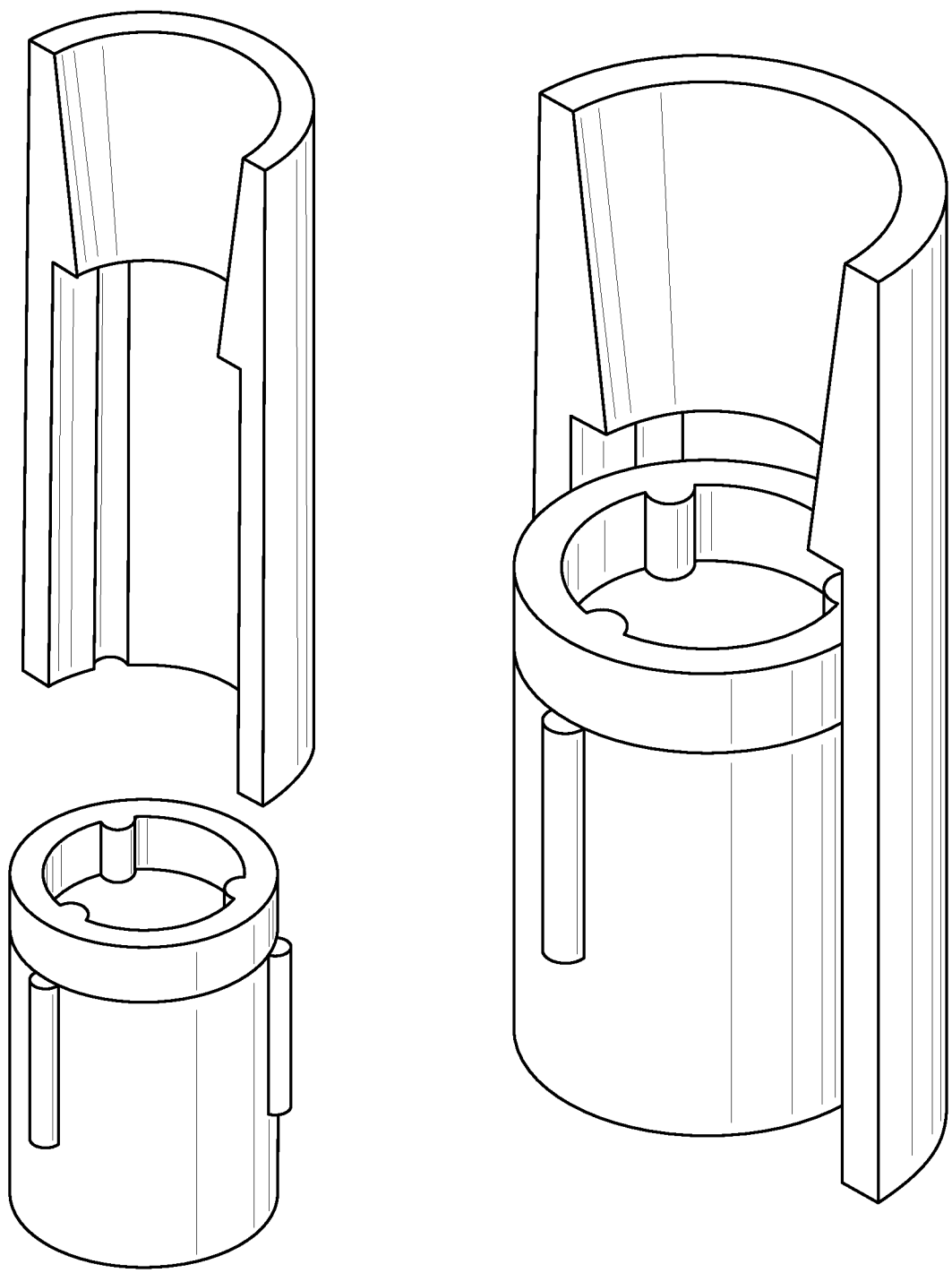
Figure 11A:
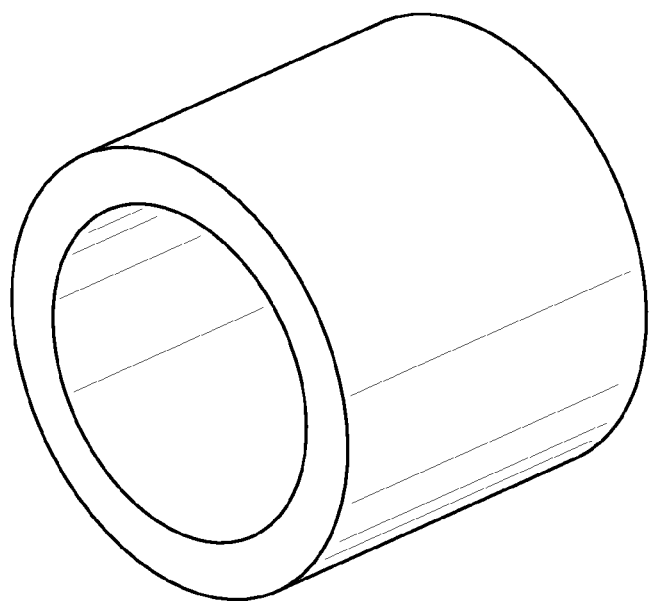
Figure 11B:
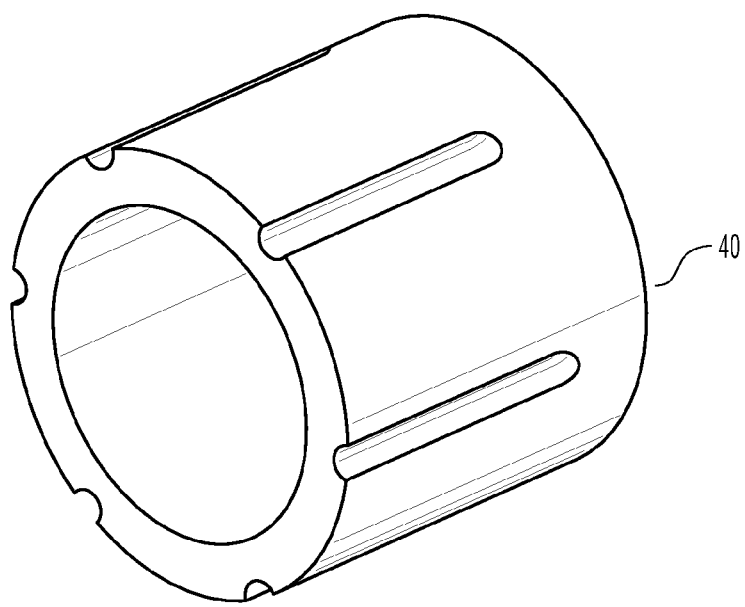
Figure 12A:
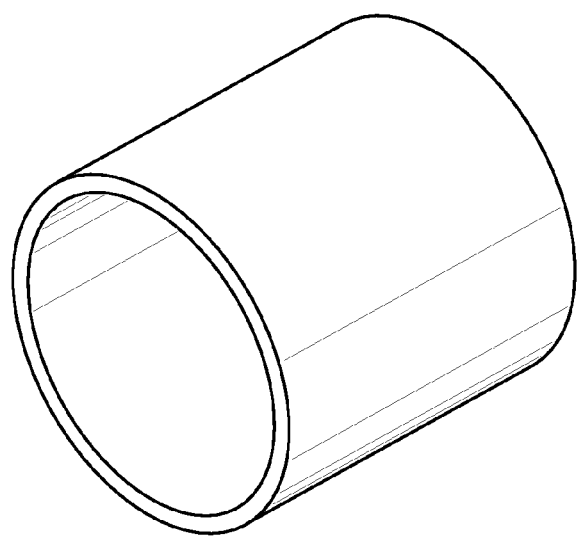
Figure 12B:
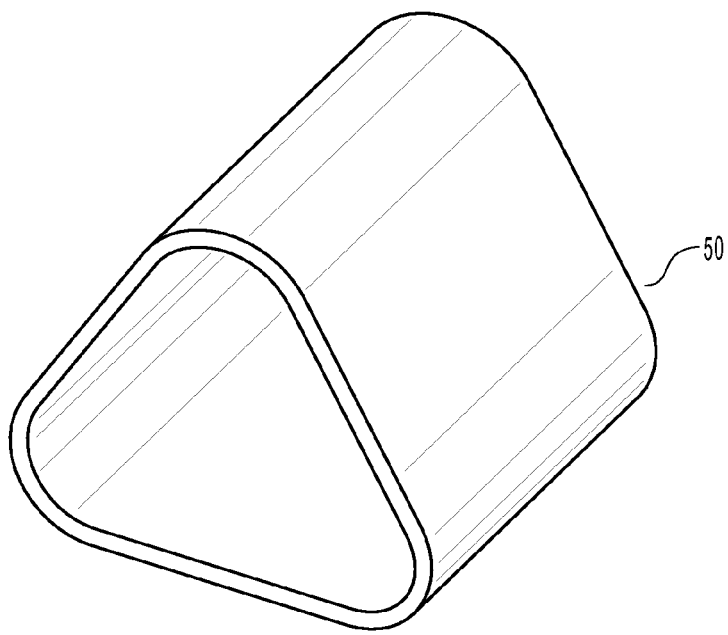
Figure 15:
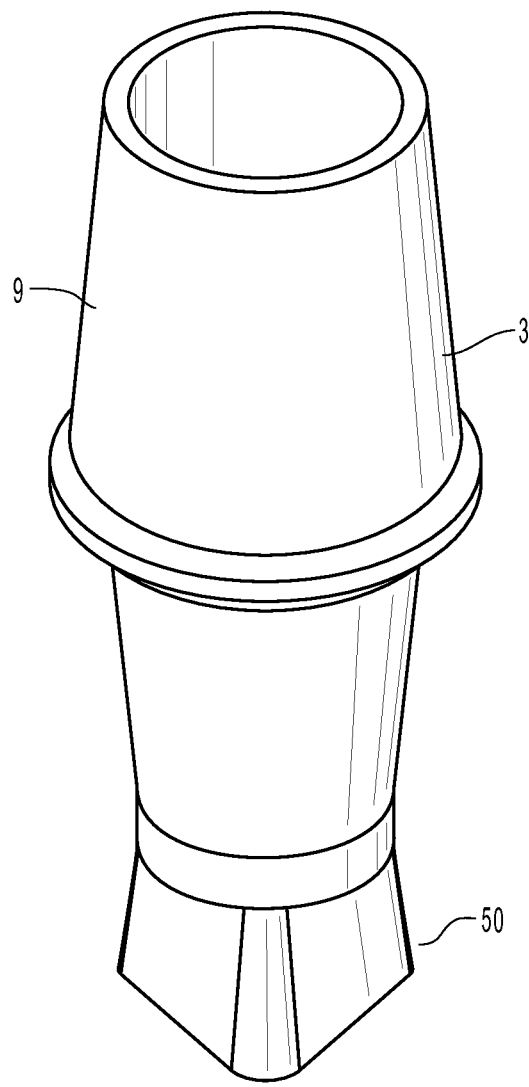
Figure 20:
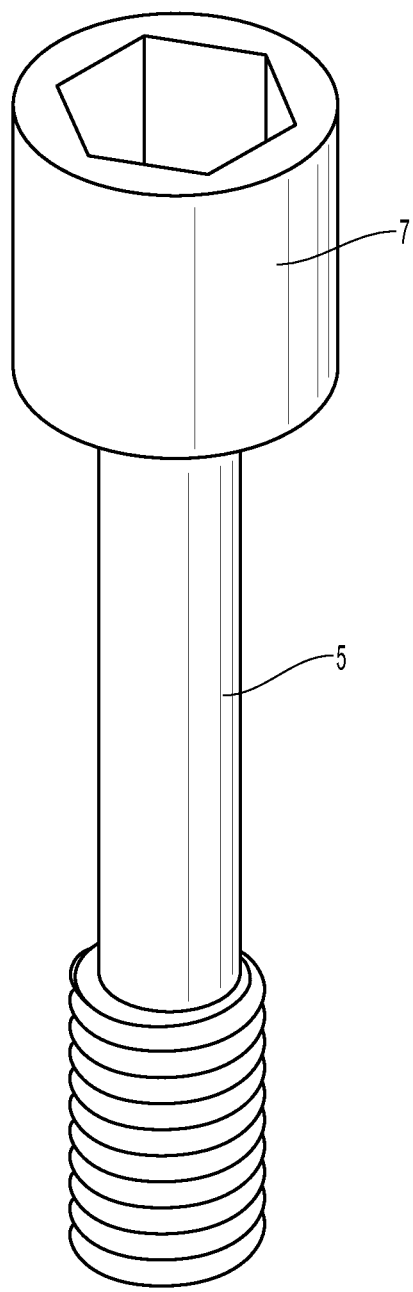
Figure 21:
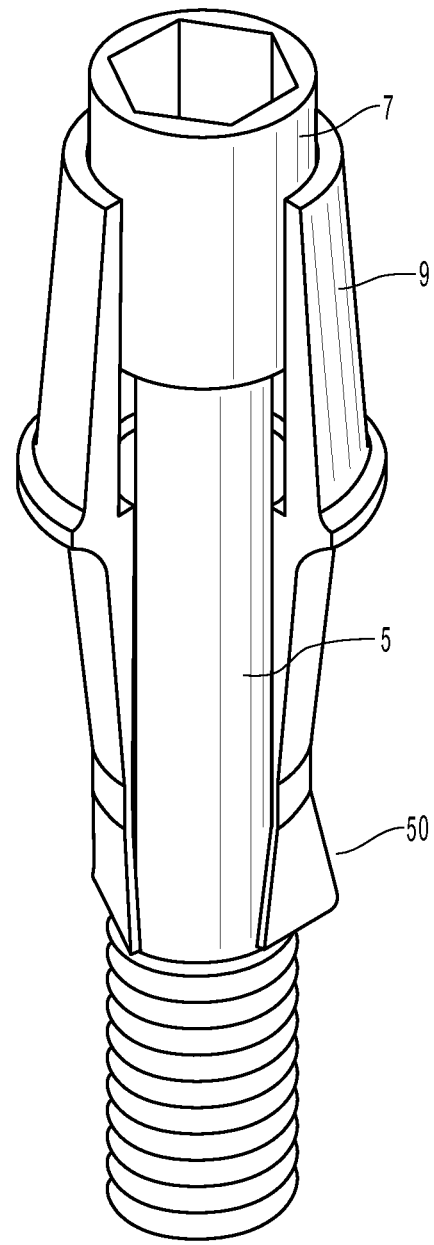

FIG. 3 shows an alternative embodiment of a dental implant according to the prior art FIG. 4 shows a further embodiment of a dental implant according to the prior art, FIG. 5 shows yet another embodiment of a dental implant according to the prior art, FIG. 6 shows a dental implant with a two-piece mounting part, FIG. 7 shows an alternative embodiment of a dental implant with a two-piece mounting part, FIG. 8 shows a laboratory implant with an integrated tool, FIG. 9 shows an exploded view of a multi-part laboratory implant, FIG. 10 shows an alternative view of the multi-part laboratory implant according to FIG. 9, FIG. 11A shows a mounting part tube before being shaped by a tool, FIG. 11B shows the mounting tube of FIG. 11A after being shaped by a tool, FIG. 12A shows a mounting part tube before being shaped by a tool, FIG. 12B shows the mounting part tube of FIG. 12A after being shaped by a tool, FIG. 13 shows the mounting part with a round apical tube, FIG. 14 shows the mounting part with an indexed apical tube, FIG. 15 shows the mounting part with an alternative embodiment of an indexed apical tube, FIG. 16A shows a laboratory implant and a mounting part, prior to insertion of the mounting part into the laboratory implant, FIG. 16B shows the tool of the laboratory implant in FIG. 16A, FIG. 17A shows the laboratory implant of FIG. 16A, with the mounting part inserted therein, prior to shaping of the mounting part tube by the laboratory implant tool, FIG. 17B shows an alignment of the mounting part tube and the laboratory implant tool of FIG. 17A prior to shaping of the tube, FIG. 18A shows the laboratory implant of FIG. 16A, with the mounting part inserted therein, with the laboratory implant tool shaping the mounting part tube, FIG. 18B shows an alignment of the mounting part tube and the laboratory implant tool of FIG. 18A, when shaping the mounting part tube, FIG. 19A shows a laboratory implant and a mounting part, after shaping of the mounting part tube and withdrawal of the mounting part from the laboratory implant, FIG. 19B shows the shaped mounting part tube of FIG. 19A, FIG. 20 shows a screw having a threaded shank which is reduced in diameter, and FIG. 21 shows the mounting part with a screw.

The same parts have been given the same reference numerals in all the figures.

The known dental implants according to FIGS. 1 to 5 each comprise the post part 2 which can be introduced into a jawbone and a mounting part 3 assigned thereto, on which a dental prosthesis piece can be mounted. In contrast to these known dental implants, the dental implant of the invention according to FIGS. 1 to 5 is designed with the aim that the rotary positioning of the upper implant structure, in particular the dental prosthesis piece to be mounted, with respect to the longitudinal axis of the post part 2 can indeed in principle be chosen freely, but this can be effected in a first working step outside the patient's mouth and therefore independently of the actual insertion of the implant. The aim here is that a dental technician ultimately determines in the laboratory, in the manner of a suitable prefabrication, the rotary adjustment of the upper implant structure depending on the desired orientation taken beforehand from the patient's mouth and therefore aligned as required. In this context, on introduction of the implant into the patient's mouth in the manner of indexing, only a small number of positionings are still possible, so that the dentist automatically chooses the correct positioning when integrating the dental prosthesis, and costly fine adjustments or the like during the treatment in the patient's mouth are therefore not necessary. For this purpose, the mounting part 3 is worked accordingly at the apical end in the laboratory according to the indexing of the post part fitted in the patient's jaw.

If the post part inserted into the patient's jaw does not have any indexing possibilities, in the variant of FIGS. 6 and 7 a first mounting part is initially screwed into the post part in the patient's mouth. This first mounting part is formed oclussally such that it allows an indexing of the second mounting part which is screwed on or in. In this respect, for example a square or hexagonal occlusal end of the first mounting part is possible. For processing and aligning the second mounting part, a gypsum model of the post part with the first mounting part screwed on is initially made. Then in the laboratory, i.e. outside the patient's mouth, the dental technician can establish the position and alignment of the second mounting part by integrating the mouldings which correspond to the first mounting part into the apical end of the second mounting part. This can be achieved by means of cutting, shaping or stamping tools. A second mounting part worked thus simplifies the alignment of the mounting part in the patient's mouth, since only a limited number of possibilities is available as a function of the indexing. Furthermore, after the second mounting part has been screwed into the first mounting part, said first mounting part can no longer rotate in the patient's mouth.

The second mounting part (31) shown in FIG. 6 does not yet have the moulding corresponding to the first mounting part and therefore, after insertion into the patient's mouth, is also able to be displaced rotatorily in relation to the post part and thus to the entire jaw. Furthermore, the treating dentist has to make a fine adjustment to the rotatory orientation during the treatment in the patient's mouth. In contrast to this, the second mounting part (31) shown in FIG. 7 has a corresponding moulding which, when inserted and screwed into the first mounting part, prevents a rotatory movement by the second mounting part.

The embodiment according to FIG. 8 shows a one-piece laboratory implant which comprises a tool (24) used for indexing. In the embodiment according to FIG. 8, this tool is configured for cutting the mounting part, but it could also be a shaping tool. As a result of inserting a mounting part into the guide shaft (22) of the laboratory implant and subsequent screwing down, the mounting part is machined and thus indexed accordingly by the tool.

FIG. 9 shows an exploded view of a multi-part laboratory implant. For reasons of clarity, the outer sheath of the implant is shown in an axial section. The laboratory implant has a tool which can be displaced in relation to the axis of the laboratory implant and is provided with a number of elements which have a shaping effect in the embodiment. However, it is also possible for the tool to contain, additionally or exclusively, cutting elements. The embodiment according to FIG. 10 shows a multi-part laboratory implant in an axial section. When inserted into the outer sheath of the implant, mouldings on the outside of the tool engage in mouldings, provided for this purpose, on the inside of the outer sheath. This prevents the tool from turning about the axis of the laboratory implant.

If the indexing of the mounting part is achieved by a shaping process, two application possibilities are provided as a function of the degree of plastic deformation. In a shaping process with a high degree of plastic deformation, the main deformation of the component is based on the fact that the forming or shaping tool penetrates the surface and as a result, the material located there is displaced. This results in a partial compression of the shaped material. An embodiment of a shaped tube having an indexing 40 resulting from a high degree of plastic deformation is shown in the illustration in FIG. 11B. In a shaping process with a low degree of plastic deformation, the main deformation of the component is based on the fact that material to be shaped is bent by the tool or is positioned around a second tool. The material is not usually compressed. In this respect, it is possible for the tube which is to be worked to penetrate into a shaping tool having, for example a round, symmetrical or other internal geometric shape or for this tube to be pushed over a tool having a correspondingly configured external geometric shape. The embodiment of a shaped tube having an indexing 50 resulting from a low degree of plastic deformation is shown in the illustration in FIG. 12B.

Therefore, to index a mounting part in relation to a post part, a variably configured tube having a round, angular or other external geometric shape can be integrally formed apically on the mounting part. A mounting part of this type is shown in FIG. 13. This tube can be shaped by means of one or more shaping tools and thus can be indexed with respect to a post part. In the mounting parts shown in FIGS. 14 and 15, the apically formed tube has been processed on the one hand by a shaping process with a high degree of plastic deformation (FIG. 14) and on the other hand by a shaping process with a low degree of plastic deformation (FIG. 15).

The energy required for indexing the mounting part can be provided, for example in the form of electrical energy, mechanical energy by for example excess pressure systems and vacuum systems, rotatory and/or translatory deflections or by the dental technician's muscle power. To avoid having to provide an additional device and a further working step not included in the standard procedure of making a dental implant, an integration of the indexing process into existing tools or working steps is therefore particularly favourable. This can reduce not only the costs of the necessary devices and materials, but also the working time of the dental technician, which can lead to a greater acceptance in the dental or implantology market. An integration of this type of the indexing process, into the conventional working procedure of the dental technician should therefore preferably take place during the attachment of the mounting part in the laboratory implant for further processing of the superstructure. In this respect, the laboratory implant is intentionally configured as a single-part or multi-part shaping or cutting tool. The tool can be rigidly connected to the laboratory implant or can be integrated therein or even connected movably therewith. Before the superstructure is processed, the mounting part is inserted detachably up to a final stop or end position in the direction of the implant axis in an implant configured in such a manner, is aligned rotatorily and connected detachably to the implant by a screw or clamping connection. The mechanical energy applied for this purpose while screwing in, driving in or, for example pressing in is used intentionally to achieve the indexing of the mounting part or of the apically integrally moulded tube. The laboratory implant preferably has at least one movable tool.

In most cases, the mounting part is screwed together with the post part either directly, in the form of an apically integrally moulded threaded part, or via a connecting screw. If the force required for shaping the indexing is generated by the mechanical work during the screwing-in procedure, restrictions arise in relation to the magnitude of the useful force due to the system-dependent dimensions of the mounting part. The connecting screws have a diameter of approximately 1 mm to 2.5 mm or at most up to 3 mm. Consequently, the degree of deformation to be achieved is relatively low. In the case of deformation with a high degree of plastic deformation, this means that the processing tool can only penetrate slightly (less than 0.5 mm, less than 0.3 mm, less than 0.1 mm or less than 0.1 mm) into the surface. In the case of deformation with a low degree of plastic deformation, this means that the material to be shaped can only have a small wall thickness (less than 0.3 mm, advantageously less than or equal to 0.2 mm and in particular less than or equal to 0.1 mm). For such an indexing of the mounting part with only a small wall thickness or a small formation, the application of force may result, however, in a reduction in the protection against rotation of the mounting part since the risk of damage to the indexing and to the mounting part is increased. In addition, when exerted forces tip the mounting part, said forces are transmitted from the connecting screw to the apically arranged, indexed part of the mounting part and can thus lead to the apical end of the mounting part breaking.

Figure 1:
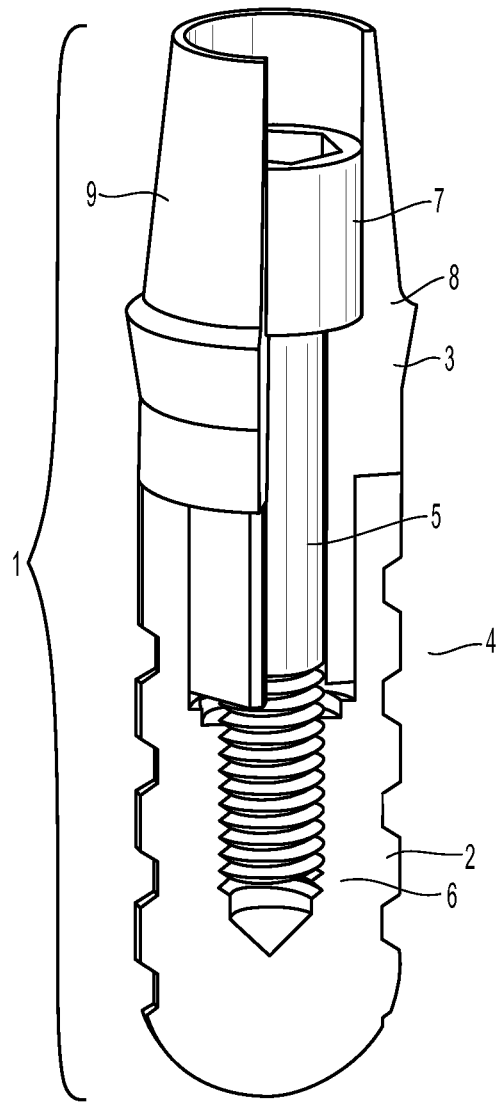
FIG. 1 shows a dental implant according to the prior art.
Figure 2:
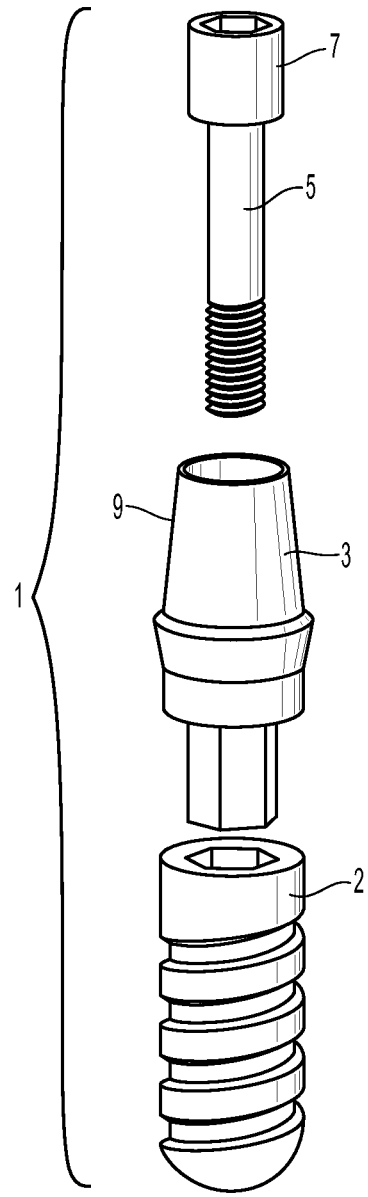
FIG. 2 shows the dental implant of FIG. 1 in an exploded view.

The connection between the post part and the mounting part is provided in many implant systems at the contact point between post part and mounting part as a blunt connection of two interlocking mouldings or integral mouldings (see FIG. 1 and 2). In such systems, the indexing also acts for the most part as a rotation protection means for the mounting part against as undesirable twisting in the patient's mouth. This anti-rotation means can be achieved alternatively or additionally by a significantly higher pretension of the connecting screw. The increase in pretension required for this purpose is, however, not possible, or only possible to a limited extent, with the present state of development with a titanium screw or a screw made of a titanium alloy in view of the stresses arising in the mouth. A reliable anti-rotation means can be provided by a conical configuration of the contact surfaces between the post part and the mounting part (FIG. 4). The static friction increased by this conical configuration and the gap-free interlocking of the post part prevents relative movements between mounting part and post part during the stresses which normally arise in the mouth. This means that the indexing formed apically on the mounting part for the post part serves only as a transfer and positioning aid and is not exposed to any, or hardly any, forces and/or torque. Thus, the configuration of a tube which is integrally formed apically on the mounting part and preferably has a low wall thickness (less than 0.3 mm, advantageously less than or equal to 0.2 mm and in particular less than or equal to 0.1 mm) and which is shaped by a plastic deformation (cold and/or hot deformation) such that it can be used as an indexing with respect to the post part, has proved to be particularly favorable when combined with a conical connection between the post part and mounting part.

The combination of a variable indexing with a conical connection configured on the mounting part to the post part or the laboratory implant has proved to be particularly favourable, since the mounting part can be fixed in a self-centring manner and thus very precisely on the implant by means of the conical connection. To further promote this process, the movable * is pressed or positioned apically in the laboratory implant by a mechanism and preferably by a spring in the apical direction. After the mounting part has been inserted into the implant, the mounting part is drawn into the implant due to the resilience, while tightening the connecting screw, and it thus centres itself independently in the implant. By tightening the connecting screw, the tool which can move in a translatory manner in the direction of the implant axis moves towards the mounting part from an apical direction. With a suitable configuration of the spring constants, the mounting part is initially pressed into the implant with a force of at least 10 N, preferably more than 20 N and in particular more than 40 N, before the tube integrally formed apically on the mounting part starts to be shaped as the force increases due to the tightening of the connecting screw. The laboratory implant and/or the mounting part has a stop against which the movable tool impacts in order to prevent one of the components from breaking upon further tightening of the connecting screw. If a fine-pitch thread is used for the connecting screw and the movable tool in the implant, i.e. a thread with a smaller pitch than is used for conventional screws (for example, according to DIN), the force used for shaping the mounting part can be significantly increased. A fine-pitch thread of this type can also be used in the post part. The indexing of the mounting part by a tool (30) integrated in the laboratory implant (20) is shown in the embodiment in FIG. 16 to FIG. 19.

Due to suitable dimensioning of the internal diameter of the tube formed integrally on the mounting part in relation to the screw shank diameter, a further advantage can be achieved during the integration of the mounting part into the post part in the patient's mouth. A pre-condition of this is that the screw shank is smaller in diameter compared to the external diameter of the thread. It is preferably dimensioned in relation to the diameter of the root of the thread or slightly smaller than this. A connecting screw of this type is shown in FIG. 20. In the case of the mounting part shown in FIG. 21 with an inserted connecting screw, the diameter of the apically integrally moulded tube is smaller than the thread diameter of the connecting screw. This is achieved in that the shape of the apically integrally moulded tube is altered. This is carried out, for example by deforming the originally round tube into a triangular tube with rounded-off corners. This reduces the passage area of the tube. A connecting screw from FIG. 19 inserted into the mounting part before shaping can consequently no longer be removed after deformation from the mounting part without breaking. The thread external diameter and shank diameter of the connecting screw have to be coordinated with the shape and diameter of the tube before and after deformation, so that the screw can be inserted into the mounting part before the tube is deformed, but after deformation can no longer fall out, but is nevertheless mounted rotatably. In this manner, the connecting screw can be secured against undesirably falling out of the mounting part and possibly being swallowed by the patient while being fitted, integrated or removed.

The tube integrally formed apically on the mounting part preferably consists, together with the mounting part, of one part and is preferably produced from a continuous blank or semi-finished product. However, the tube can also consist of a different metal and/or a different semimetal and/or of a non-metal, unlike the rest of the mounting part. The material of the tube is then preferably softer than that of the mounting part. If the tube attached apically to the mounting part consists of a different component and/or of a different material, they can be attached to the mounting part, for example by screwing, riveting, clamping, adhesively bonding, soldering or welding.

To ensure a reproducible shaping of the tube integrally formed apically on the mounting part or of the mounting part itself, the tool which can be moved in the laboratory implant and/or the laboratory implant itself should consist of a harder material than the mounting part and/or the tube formed integrally on the mounting part. Individual tools of the laboratory implant or the laboratory implant itself, but in particular the movable tool should preferably be additionally subjected to a hardness increasing process after they have been shaped. This hardening process can be superficial and can affect only part of the tool or the entire tool. While shaping the tube, the use of relatively hard materials can prevent the tool, movable in the implant, or the implant itself from becoming deformed or exhibiting an appreciable abrasion. Consequently, the laboratory implant can be used many times and the reproducibility of the formed final shape of the tube can be improved.

The invention claimed is:

1. An indexing device for indexing a dental implant, comprising
 a laboratory implant having a tool configured for working on the external cross-section of a mounting part, wherein
 said laboratory implant has an orientation and geometric form that corresponds to an orientation and geometric form of an impression of a post part as implanted in a given jaw bone, and
 said laboratory implant is configured to receive and index said mounting part while said laboratory implant is embedded in a mold of said given jaw bone.

2. The indexing device according to claim 1, wherein the material hardness of the tool is greater than that of grade 5 titanium.

3. The indexing device according to claim 1, wherein the said laboratory implant comprises ceramic constituents and/or hard metal constituents.

* * * * *